US008723936B2

(12) United States Patent
Amling et al.

(10) Patent No.: US 8,723,936 B2
(45) Date of Patent: May 13, 2014

(54) WIRELESS CAMERA COUPLING WITH ROTATABLE COUPLING

(75) Inventors: Marc R. Amling, Santa Barbara, CA (US); Hans David Hoeg, Arcadia, CA (US); David Chatenever, Santa Barbara, CA (US); Charles E. Ankner, Santa Maria, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 755 days.

(21) Appl. No.: 12/879,380

(22) Filed: Sep. 10, 2010

(65) Prior Publication Data

US 2011/0193948 A1    Aug. 11, 2011

Related U.S. Application Data

(63) Continuation-in-part of application No. 12/533,545, filed on Jul. 31, 2009, now Pat. No. 8,599,250, which is a continuation-in-part of application No. 11/542,461, filed on Oct. 3, 2006, now Pat. No. 8,194,122, which is a continuation-in-part of application No. 10/095,616, filed on Mar. 12, 2002, now Pat. No. 7,289,139.

(51) Int. Cl.
*H04N 7/18* (2006.01)
*H04N 9/47* (2006.01)

(52) U.S. Cl.
USPC ............................................. 348/65

(58) Field of Classification Search
USPC .................... 348/61, 65; 600/112; 455/562.1; 358/1.15
See application file for complete search history.

(56) References Cited

U.S. PATENT DOCUMENTS

| 4,478,212 A * | 10/1984 | Asano ........................... 600/112 |
| 4,777,947 A | 10/1988 | Zwick |
| 5,492,527 A | 2/1996 | Glowa et al. |
| 5,592,727 A | 1/1997 | Glowa |
| 5,630,180 A | 5/1997 | Kusaka |
| 5,669,921 A | 9/1997 | Berman et al. |
| 5,810,858 A | 9/1998 | Berman et al. |

(Continued)

FOREIGN PATENT DOCUMENTS

| DE | 19723442 A1 | 2/1998 |
| EP | 0534198 A2 | 3/1993 |

(Continued)

OTHER PUBLICATIONS

Extended European Search Report; EP 07 01 9378; Feb. 8, 2008; 4 pages.

(Continued)

*Primary Examiner* — Allen Wong
(74) *Attorney, Agent, or Firm* — St. Onge Steward Johnston & Reens LLC

(57) ABSTRACT

A system for wirelessly powering various devices positioned on an endoscope, including, for example, a light source, various electronics including an imager and/or a memory device. The endoscope is coupled to a camera where the endoscope may be rotated relative to the camera when coupled thereto. The system is further provided such that video signal processing parameters are automatically set for an endoscopic video camera system based upon characteristics of an attached endoscope, with reduced EMI and improved inventory tracking, maintenance and quality assurance, and reducing the necessity for adjustment and alignment of the endoscope and camera to achieve the data transfer.

32 Claims, 5 Drawing Sheets

(56) References Cited

U.S. PATENT DOCUMENTS

| | | | |
|---|---|---|---|
| 5,896,166 A | | 4/1999 | D'Alfonso et al. |
| 5,910,776 A | | 6/1999 | Black |
| 6,053,928 A | | 4/2000 | Van Wyk et al. |
| 6,092,722 A | | 7/2000 | Heinrichs et al. |
| 6,141,037 A | * | 10/2000 | Upton et al. .............. 348/65 |
| 6,217,598 B1 | | 4/2001 | Berman et al. |
| 6,295,082 B1 | | 9/2001 | Dowdy et al. |
| 6,313,868 B1 | | 11/2001 | D'Alfonso et al. |
| 6,328,752 B1 | | 12/2001 | Sjostrom et al. |
| 6,364,827 B1 | | 4/2002 | Irion et al. |
| 6,419,684 B1 | | 7/2002 | Heisler et al. |
| 6,436,032 B1 | | 8/2002 | Eto et al. |
| 6,638,212 B1 | | 10/2003 | Oshima |
| 6,882,868 B1 | * | 4/2005 | Shattil .............. 455/562.1 |
| 6,968,610 B2 | | 11/2005 | Nagao et al. |
| 7,237,990 B2 | | 7/2007 | Deng |
| 7,247,161 B2 | | 7/2007 | Johnston et al. |
| 7,273,483 B2 | | 9/2007 | Wiener et al. |
| 7,289,139 B2 | | 10/2007 | Amling et al. |
| 7,887,559 B2 | | 2/2011 | Deng et al. |
| 2001/0052930 A1 | * | 12/2001 | Adair et al. .............. 348/65 |
| 2002/0080392 A1 | * | 6/2002 | Parvulescu et al. .......... 358/1.15 |
| 2002/0161385 A1 | | 10/2002 | Wiener et al. |
| 2003/0145646 A1 | | 8/2003 | Henry et al. |
| 2003/0174205 A1 | | 9/2003 | Amling et al. |
| 2004/0064019 A1 | | 4/2004 | Chang et al. |
| 2004/0252188 A1 | | 12/2004 | Stantchev et al. |
| 2004/0267297 A1 | | 12/2004 | Malackowski |
| 2005/0187537 A1 | | 8/2005 | Loeb et al. |
| 2006/0095096 A1 | | 5/2006 | DeBenedictis et al. |
| 2006/0149126 A1 | | 7/2006 | Ertas et al. |
| 2006/0171693 A1 | | 8/2006 | Todd et al. |
| 2007/0030345 A1 | | 2/2007 | Amling et al. |
| 2009/0030278 A1 | | 1/2009 | Minakuchi |
| 2010/0004523 A1 | | 1/2010 | August et al. |
| 2010/0141744 A1 | | 6/2010 | Amling et al. |

FOREIGN PATENT DOCUMENTS

| | | |
|---|---|---|
| EP | 1155654 A1 | 11/2001 |
| EP | 1347638 A1 | 9/2003 |
| EP | 1424036 A1 | 6/2004 |
| EP | 1759629 A1 | 3/2007 |
| EP | 1767140 A1 | 3/2007 |
| JP | 59069720 A | 4/1984 |
| JP | 2001046326 A | 2/2001 |
| JP | 2001327459 A | 11/2001 |
| JP | 2003325432 A | 11/2003 |
| JP | 2004174008 A | 6/2004 |
| JP | 2006254974 A | 9/2006 |
| WO | 9729678 A2 | 8/1997 |
| WO | 2005115106 A2 | 12/2005 |
| WO | 2009027672 A1 | 3/2009 |
| WO | 2009060460 A2 | 5/2009 |

OTHER PUBLICATIONS

International Search Report and Written Opinion of the International Searching Authority; PCT/US09/43733; Jun. 18, 2009; 8 pages.

Japanese Office Action; Application No. 2003-066189; Aug. 22, 2006; 2 pages.

Microchip, 1K/2K/4K 1.8V Microwave Serial EEPROM, Microchip Technology Inc., 1996, 12 Pages.

Medical Connectivity Consulting, "New RFID standard Rubee has health care applications", http://medicalconnectivity.com/2006/09/27/new-rfid-standard-rubee-has-health-care-application, Sep. 27, 2006, 5 Pages.

European Search Report; Application No. EP 10 17 0427; Sep. 30, 2010; 8 pages.

European Search Report; Application No. EP 11 17 9304; Issued: Dec. 20, 2011; Mailing Date Jan. 1, 2012; 6 pages.

* cited by examiner

WIRELESS CAMERA COUPLING WITH ROTATABLE COUPLING

CROSS-REFERENCE TO RELATED APPLICATIONS

This application is a continuation-in-part application of U.S. patent application Ser. No. 12/533,545 filed Jul. 31, 2009, now U.S. Pat. No. 8,599,250 which is a continuation-in-part application of U.S. patent application Ser. No. 11/542,461 filed Oct. 3, 2006, now U.S. Pat. No. 8,194,122 which is a continuation-in-part application of U.S. patent application Ser. No. 10/095,616 filed Mar. 12, 2002, now U.S. Pat. No. 7,289,139 issued on Oct. 30, 2007.

FIELD OF THE INVENTION

The invention relates to endoscope video camera systems, where the video camera electronically identifies an attached endoscope and automatically sets system parameters in accordance with certain endoscope parameters and wirelessly provides power to the endoscope. The endoscope may be electronically identified for manipulating, (i.e., reading information from, updating and then writing information to the endoscope) for the purposes of endoscope use and maintenance, inventory tracking and control, and monitoring of various other endoscope parameters. Further, the endoscope may be coupled to and is rotatable relative to the camera.

BACKGROUND OF THE INVENTION

An endoscope is an elongated, tubular structured medical device that is inserted into body cavities to facilitate visualization and examination by medical professionals. The endoscope includes a telescope with an objective lens at its distal end. The telescope includes an image-forwarding system, which in rigid endoscopes is typically a series of spaced-apart lenses. In flexible endoscopes, typically, the image-forwarding system is a bundle of tiny optical fibers assembled coherently.

Typically, at the proximal end of the image-forwarding system is an ocular lens that creates a virtual image for direct human visualization. Often a camera means, such as a charge coupled device (CCD) chip or a CMOS device is mounted to the endoscope. The camera means receives the image and produces a signal for a video display. While surgeons can, and often do, look directly into the endoscope through an ocular lens, it is more common for them to use an attached camera and observe an image on a video screen. In conventional and video camera arrangements, the camera (hereinafter referred to as a "camera head") is usually detachably connected to the endoscope. A camera control unit (CCU) is employed to provide, among other controls, a link between the camera head and the video display.

As the camera head is detachable from the endoscope, this necessitates a coupling mechanism to transmit, for example, data and/or optical energy (i.e. illuminating light) between the endoscope and detachable camera. However, it would be advantageous to eliminate the need for a coupling mechanism to transmit optical energy between the endoscope and detachable camera as misalignment, dirt/debris and damage to the optical path at the coupling location can reduce the efficiency of the optical path. However, the generation of optical energy in the endoscope has not been feasible because to the corresponding increase in weight of the endoscope when a power source (e.g. a battery) is positioned on the endoscope. Accordingly, a system that provides for the generation of optical energy in the endoscope is desired that does not significantly increase the weight and size of the endoscope is desired.

Some video endoscope systems have provided a coupling mechanism between the endoscope and the camera that includes, for example, a stem/receptacle arrangement for transmitting illuminating light from the camera to the endoscope and a stem/receptacle arrangement for transmitting image data from the endoscope to the camera. However, this arrangement does not necessarily provide an easy way to pan the endoscope. For instance, as the endoscope and camera are locked together, the surgeon has to rotate his/her wrist to achieve a panning effect. This only allows for limited rotation, i.e. a wrist cannot be rotated indefinitely, and causes disorienting image spin as the camera and endoscope are rotated as a single unit during panning.

Various systems have tried to address the issue of allowing relative rotation between the endoscope and camera with limited success. A challenge faced by designers is that as the shaft rotates relative to the camera, either the illumination system or the image optical system has to rotate around a central axis. Typically the image optical system is placed in the center, i.e. defines the central axis of the endoscope, and the illumination system is eccentric to the image optical system, causing the illumination system to move concentrically about the central axis of the endoscope as the shaft is rotated/panned. This rotatable illumination system makes it difficult to transfer light from the camera to the endoscope. One design has the portion of the illumination system that is housed in the camera be movable to follow the motion of the shaft. This requires the light conduit to wind up inside the camera head. It cannot, however, be wound indefinitely, and therefore it is necessary to limit the panning range. This limitation can be annoying to surgeons because once the limit is reached, the device has to be panned back the opposite direction to reach the viewing destination. Additionally, mechanical wear associated with repeated winding and unwinding of the illumination conduit is problematic, as well as "sealing" any moving parts to prevent undesired "leakage" of high intensity light from coupling.

Another design is based on what could be called an illumination slip ring where fibers are splayed out in a circular arrangement and will thus receive light regardless of rotational position. One could also use LEDs arranged in a circle. This optical slip-ring design is unfortunately difficult to manufacture and typically has problems of low efficiency, excessive and/or unsafe heat build-up, and non-uniform illumination.

Because of these many problems, endoscope designers have looked at placing the illumination source, which traditionally has been an external bulb providing light through an external light guide, inside the endoscope shaft. LEDs have been used to provide illumination. However, utilizing LEDs requires electrical power to the LEDs themselves. Arguably, electrical slip rings are more tried and true than optical slip rings, but electrical slip rings typically have problems with wear, electromagnetic noise, and reliability. Further, in a surgical/medical setting, there is the additional safety concern of electrical power transfer across an open rotating interface. The main drawback with a design which puts the light source in the endoscope however, is that it is not compatible with current endoscopic systems already in the field.

It should further be noted that endoscopes come in a variety of sizes for particular applications and surgical procedures. The telescope lens system may have a variety of optical properties. For example, the objective lens may include a prism whereby the image viewed is at some angle with respect to that of the axis of the telescope. Also, different endoscopes may have different fields of view (FOV). These and other variations affect the optical properties of particular endoscopes.

As above noted, the camera head is usually detachable from the endoscope, and is often conveniently constructed so as to be attachable to a variety of endoscopes having differing optical properties. For this reason, a CCU receiving a video signal from an attached camera head will need to know the endoscope optical properties in order to present an optimized image on the video monitor. Currently, the settings of the camera head and CCU are manually adjusted to the endoscope's optical properties.

It would be advantageous to simplify the task of using the endoscope and video camera system by eliminating the need to make manual adjustments to the camera head and/or CCU in order to optimize the video camera system settings for an attached endoscope.

To ensure optimal video system operation utilizing a particular endoscope, it is also necessary that the endoscope undergo periodic scheduled and unscheduled maintenance. Further, most endoscope manufacturers require their products to be maintained properly to assure reliable, accurate and precise functionality. This enhances the manufacturer's reputation and the reliance of health care professionals on the manufacturer's products. From a manufacturer's perspective, it is important that only factory authorized personnel service their products; however, it is a reality in the marketplace that some medical facilities may use unauthorized repair services. It is to a manufacturer's advantage to discourage such suboptimal maintenance because if maintenance is performed incorrectly, medical personnel may attribute problems caused by the incorrectly performed maintenance to the product and/or manufacturing design.

Related to the maintenance of the endoscope are the usage characteristics of the endoscopes. For a manufacturer, how its products are used is valuable information. A manufacturer may want to know, for example, how often each product is used, the elapsed time of each use, the maintenance history of the product, and so on. These factors can impact future endoscope design related to durability, reliability, components and materials used in the manufacturing process.

It is known in the art to utilize electronic sensors to record operating conditions beyond the endoscope's recognized safe operating range to which it has been subjected. Peak values for conditions such as, pressure, humidity, irradiation, and/or shock or impact loads to which the endoscope has been exposed may be recorded. Upon failure of the endoscope, this information may then be utilized to determine the probable cause of the failure.

U.S. Pat. No. 5,896,166 to D'Alfonso et al. ("the '166 patent") and U.S. Pat. No. 6,313,868 to D'Alfonso et al. ("the '868 patent"), both disclose storing camera parameters and camera use characteristics in a non-volatile memory located in the camera head and transmitting the camera parameters and camera use characteristics to a camera control unit through a data coupling upon connection of the camera unit to a camera control unit. However, neither reference discloses a system where the endoscope has a memory device located in it, so that a single camera unit may be interchanged with a plurality of endoscopes and whereupon connection of the camera unit will automatically read the endoscope parameters and use characteristics. Further, neither the '166 nor the '868 patent discloses a system where the endoscope use characteristics can be updated to log a history of the particular endoscope use. Rather, both the '166 and the '868 patents are limited to updating only the camera unit. Still further, neither the '166 nor the '868 patent discloses a system wherein the endoscope parameters and use characteristics can be read automatically through non-contact transmission.

Another problem in the field of endoscope management is that of keeping track of the many different endoscopes used throughout the facility. There have been various approaches to keeping track of the locations and inventory of endoscopes. Simple inventory control and sign-out sheets are labor intensive and inaccurate, and, as a result, are ineffective for assuring the level of scrutiny that is required for medical equipment. Further, sign-out sheets do not allow for monitoring equipment, for example, determining whether the endoscope is functioning properly or needs maintenance.

Bar codes have been used for tracking purposes. Bar coding of equipment allows identification and locating of the equipment by reading the bar code with a portable bar code scanner. However, bar coding is ineffective when the equipment has been moved since the last time that it was scanned. Moreover, the use of bar codes can require the labor-intensive step of touring the facility with one or more portable scanners in search of endoscopes. Further, bar codes, like sign-out sheets, do not allow for the monitoring of equipment, for example, determining whether the endoscope is functioning properly or needs maintenance.

It is known in the art that energy and data transmission can take place through an inductive coupling in which high frequency coils act like a loosely coupled transformer as disclosed in U.S. Pat. No. 6,092,722 to Heinrichs et al. ("the '722 patent"). The high frequency coil, when power is applied to it, produces a high frequency field, which will be imposed upon the high frequency coil of another device when brought into close proximity.

One major problem with the use of inductive coupling as disclosed in the '722 patent is that it can create unacceptable levels of electro-magnetic interference ("EMI") in the operating room environment. Electronic equipment, such as the video signals transmitted from the camera head to the camera control unit, can be particularly sensitive to EMI. Therefore, to reduce the negative effects of EMI, adequate shielding should be provided. This, however, significantly adds to the cost and manufacturing time of the device. Therefore, a system that does not produce EMI is greatly desired.

Another disadvantage with the use of inductive coupling as disclosed in the '722 patent is that it necessitates the use of inductive coils both in the endoscope and the camera head adding greatly to the size and the weight of the devices. In addition to the added size and weight of the inductive coils, the necessary shielding for the EMI produced by the inductive coils will further increase the device size and weight. Endoscopes and camera heads that are lighter, smaller and easier to handle are desired.

Another disadvantage to the inductive coupling technique as disclosed in the '722 patent is because high frequency coils act like a loosely coupled transformer, both high frequency coils should be aligned one directly on top of the other in order to achieve an effective data transfer. The inductive field created by the high frequency coils is unidirectional and therefore accurate alignment of the component is important. This situation could be very frustrating for medical professionals, having to spend time trying to accurately align the camera head and endoscope to have the video system function properly. Therefore, a system that does not require precise alignment of the components is desired.

Radio frequency identification ("RFID") has been used to locate various devices and/or equipment. However, RFID used in the operating room environment has been limited due to the large power ranges required for locating the device.

RFID utilized for locating purposes necessitates using a transceiver with as large a power range as is reasonable. A large power range, unfortunately, may cause receipt of the signal by unintended RFID receivers. That is, if an endoscope is in use in room A, it is undesirable to have unrelated endoscope equipment in room B "respond" to the transceiver. RFID has been limited to tracking the location of devices and/or equipment, facilitating only one-way communication from the device and/or equipment to the recording or tracking system.

While RFID has the advantage of having a relatively rapid read rate, one particular limitation RFID has encountered is accuracy of scans in relatively harsh environments. For example, RFID has been known to struggle with getting an accurate read through or near liquids and metals.

Therefore, a system is needed that simplifies and optimizes endoscope and video camera usage and does not interfere with sensitive electronic equipment, encourages customers to maintain the endoscope to manufacturer's parameters and provides the endoscope manufacturer with information regarding product usage and maintenance.

SUMMARY OF THE INVENTION

Accordingly, some aspects of the present invention address the aforementioned problems by providing a method and system for contactless wireless inductive power transfer from the endoscopic camera head to an onboard light source in the endoscope, which may be positioned in a handle or in the shaft of an endoscope. This scheme allows for: 1) no lateral forces or moments from a laterally connected light guide; 2) unlimited relative rotation between camera head and endoscope shaft without light guide wind-up; 3) no disorienting image rotation when panning the endoscope shaft; 4) easy and quick switching between endoscopes during a procedure; 5) compatibility with current endoscopic systems already in place in hospitals and medical centers; 6) easier troubleshooting and repair because the system is modular; and 7) robustness—single piece systems break more easily during reprocessing/sterilization because of the heavy camera/handle portion being rigidly connected to the fragile endoscope portion.

In one aspect of the invention, a system is provided including an endoscope and a detachable camera head. The endoscope is provided with a transponder/transceiver and the detachable camera head is provided with a corresponding transponder/transceiver such that electrical power is transmitted from the camera head to the endoscope. The endoscope is provided with a light source (e.g. an LED) positioned thereon, where electrical power is wirelessly transmitted from the detachable camera head to the endoscope to power the LED. It is further contemplated that not only is electrical power transmitted, but image data generated by the endoscope (e.g. via a CCD or CMOS device) may also be wirelessly transmitted from the endoscope to the detachable camera head. Still further, command and control data may be transmitted between the endoscope and the detachable camera head.

In another aspect of the invention, a system is provided such that an endoscope read/write apparatus stores and provides endoscope parameters and endoscope use history data, utilizing a detachable camera capable of accessing the endoscope parameter data and endoscope use history data, and if required, updating and rewriting endoscope use history data to the endoscope for storage. A transponder/transceiver is affixed to the endoscope, and the endoscope transponder/transceiver is capable of transmitting and receiving wireless signals. The endoscope transponder/transceiver is coupled to a memory device that stores electronic representations of the endoscope parameters and endoscope use history data, and when queried, supplies the electronic representations to the endoscope transponder/transceiver. To transmit wireless signals for communication with the endoscope transponder/transceiver, a camera transponder/transceiver is affixed to the camera and set to receive the endoscope transponder/transceiver transmitted wireless signals.

In one embodiment, the present invention utilizes wireless transponder/transceivers using either an RFID format or a standard called IEEE 1902.1, which is also known as the "RuBee" format. As such, the problems associated with inductive coupling such as radiated EMI, alignment requirements, and inability to locate the device are absent.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "coupled", "coupled to", and "coupled with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The terms "process" and "processing" as used herein each mean an action or a series of actions including, for example, but not limited to the continuous or non-continuous, synchronous or asynchronous, direction of data, modification, formatting and/or conversion of data, tagging or annotation of data, measurement, comparison and/or review of data, and may or may not comprise a program.

The terms "first" and "second" are used to distinguish one element, set, data, object or thing from another, and are not used to designate relative position or arrangement in time.

The term "resonant" interaction as used herein, is used to describe the relatively strong coupling that occurs between two substantially same-frequency objects (e.g. a transmitter/receiver), while interacting relatively weakly with other off-resonant environmental objects. "Resonant" interaction would further encompass resonant evanescent coupling where resonant coupling occurs through the overlap of non-radiative near-fields of two objects.

In one advantageous embodiment of the present invention, an endoscope video system is provided for communicating between an endoscope and a detachable camera comprising: a first transponder/transceiver is affixed to the endoscope set to transmit wireless signals containing endoscope parameters and endoscope use history data and set to receive wireless signals containing modified endoscope use history data; a second transponder/transceiver affixed to the detachable camera set to transmit wireless signals containing modified endoscope use history data, and set to receive wireless signals containing the endoscope parameters and endoscope use history data; a memory device coupled to the first transponder/transceiver having memory locations for storing the data contained in the wireless signals; and a camera control unit, coupled to the camera, for receiving and processing the endoscope parameters and endoscope use history data.

In another advantageous embodiment of the present invention, an endoscope video system is provided for the transfer of data from an endoscope comprising: a transponder/transceiver affixed to the endoscope, set to transmit wireless signals containing endoscope parameters and endoscope use history data, and set to receive wireless signals containing modified endoscope use history data; and a memory device coupled to the transponder/transceiver having memory locations for storing the data contained in the wireless signals.

In yet another advantageous embodiment of the present invention, an endoscope video system is provided for automatically adjusting to the parameters of a plurality of endoscopes, and to provide for the transfer of modified endoscope use history data comprising: a transponder/transceiver positioned on a camera head, set to transmit wireless signals containing modified endoscope use history data, and set to receive wireless signals containing endoscope parameters and endoscope use history data; and a camera control unit, coupled to the camera, for receiving and processing the endoscope parameters and endoscope use history data.

In still another advantageous embodiment of the present invention, a method is provided for communicating endoscope parameters and use characteristics from an endoscope, having a memory device and a first transponder/transceiver coupled to the memory device, to a camera control unit, and communicating modified endoscope use characteristics from the camera control unit to the endoscope comprising the steps of: storing a plurality of endoscope parameters and endoscope use characteristics in the memory device; providing a camera with a second transponder/transceiver; coupling the second transponder/transceiver to the camera control unit; retrieving the endoscope parameters and endoscope use characteristics from the memory device; transmitting a first wireless signal containing the endoscope parameters and endoscope use characteristics from the first transponder/transceiver; receiving the first wireless signal at the second transponder/transceiver; transferring the endoscope parameters and endoscope use characteristics contained in the first wireless signal from the camera head to the camera control unit; transferring modified endoscope use characteristics from the camera control unit to the camera; transmitting a second wireless signal containing the modified endoscope use characteristics from the second transponder/transceiver to the first transponder/transceiver; receiving the second wireless signal containing the modified endoscope use characteristics; and storing the modified endoscope use characteristics in the memory device memory locations.

In a further advantageous embodiment of the present invention, an endoscope video system is provided for communicating between an endoscope and a detachable camera comprising: a first transponder/transceiver attached to the endoscope for transmitting and receiving first data; a second transponder/transceiver attached to the detachable camera for transmitting and receiving second data; and a memory device coupled to the first transponder/transceiver having memory locations for storing data.

In a still another advantageous embodiment an endoscope video system for wirelessly powering an endoscope coupled to a detachable camera is provided comprising an endoscope having a receiver position thereon, the receiver receiving wireless energy and an endoscope coupling mechanism affixed to a proximal end of said endoscope. The system further comprises a camera having a transmitter positioned thereon, the transmitter wirelessly coupling to the receiver when brought in proximity thereto to transmit energy to the receiver and a camera coupling mechanism engagable with the endoscope coupling mechanism to mechanically couple the endoscope to the camera. The system still further comprises an endoscope light source positioned on the endoscope, the endoscope light source coupled to and receiving electrical power from the receiver, where the endoscope light source generates illuminating light.

In a yet another advantageous embodiment a method for wirelessly powering an endoscope coupled to a detachable camera is provided comprising the steps of positioning a receiver on an endoscope having an endoscope coupling mechanism, positioning a transmitter on a camera having a camera coupling mechanism and positioning an endoscope light source on the endoscope. The method further comprises the steps of mechanically coupling the endoscope to the camera via the endoscope and camera mechanisms and coupling the endoscope light source to the receiver. The method still further comprises the steps of wirelessly transmitting energy from the transmitter to the receiver and generating illuminating light with the endoscope light source with electrical power provided to the endoscope light source from the receiver.

The invention and its particular features and advantages will become more apparent from the following detailed description considered with reference to the accompanying drawings.

DETAILED DESCRIPTION OF THE INVENTION

Figure 1:
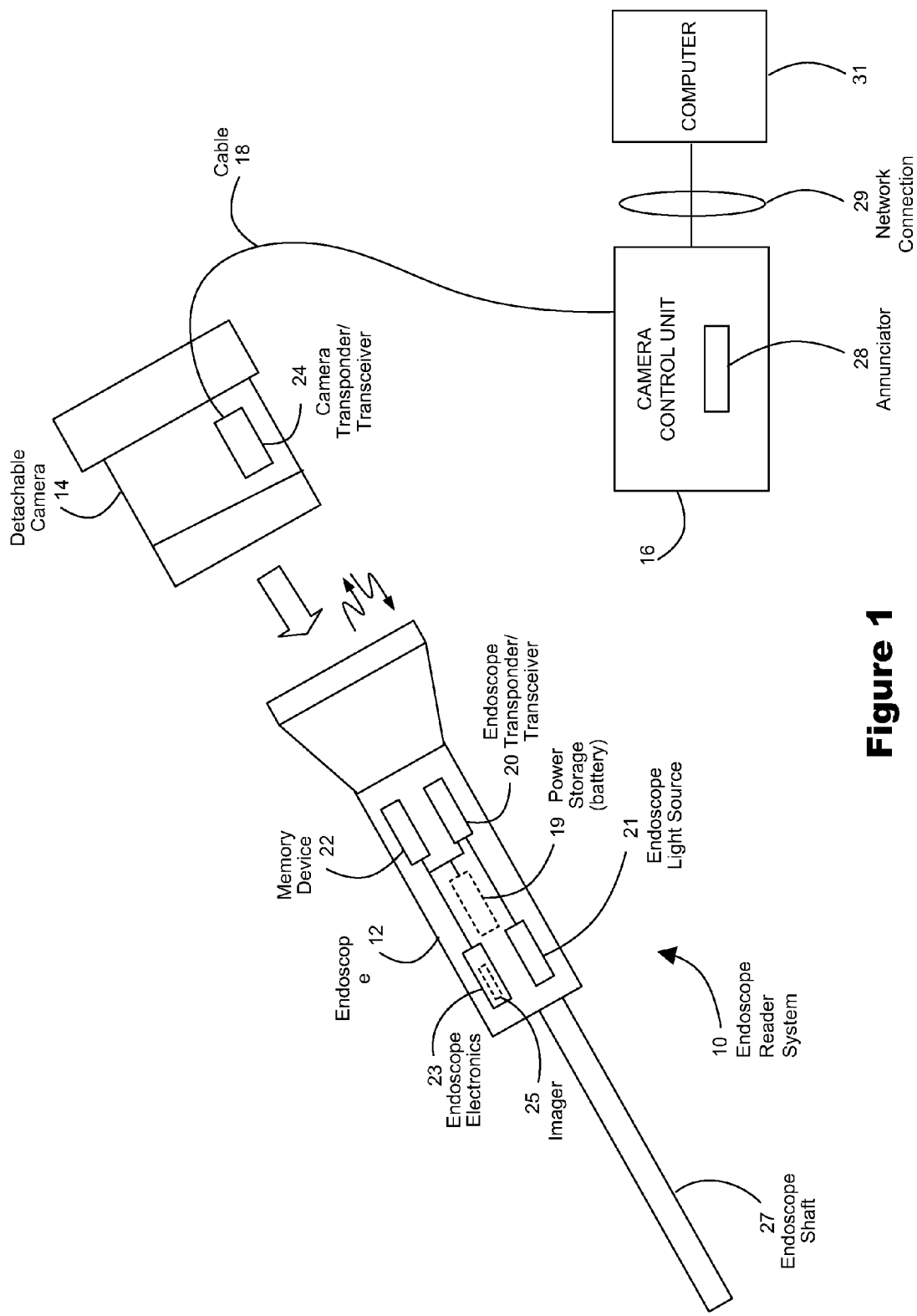
FIG. 1 is an illustration of the assembly of a detachable camera to an endoscope.

Referring now to the drawings, wherein like reference numerals designate corresponding structure throughout the views.

FIG. 1 illustrates an endoscope system 10 for wirelessly transmitting energy and data, including, for example, storing and transmitting electronic representations of endoscope characteristics. In accordance with one advantageous embodiment, an endoscope transponder/transceiver 20 is mounted on an endoscope 12 and communicates with a camera head transponder/transceiver 24 mounted on a detachable camera head 14. Endoscope transponder/transceiver 20 and camera head transponder/transceiver 24 may be one of any type of relatively short-range devices well known to those of ordinary skill in the art. Endoscope transponder/transceiver 20 and camera head transponder/transceiver 24 are set so that each is capable of both sending and receiving wireless signals to and from the other.

In one advantageous embodiment, transponder/transceiver 20 and 24 are provided as Radio Frequency (RF) transceivers capable of generating, transmitting and receiving RF signals whether RFID High-Frequency (HF) or Ultra-High Frequency (UHF).

In another advantageous embodiment, transponder/transceiver 20 and 24 may be provided to generate, transmit and receive wireless signals via a standard called IEEE 1902.1, which is also known as the "RuBee" format. Where traditional RFID tags are backscattered transponders, RuBee operates as an active transceiver. RuBee is a bidirectional, on-demand, peer-to-peer, radiating, transceiver protocol operating at wavelengths below 450 KHz. This protocol is advantageous in harsh environments with networks of many thousands of tags and may have an area range of from 10 to about 50 feet.

RuBee offers a real-time, tag-searchable protocol using IPv4 addresses and subnet addresses linked to asset taxonomies that run at speeds of 300 to 9,600 Baud. RuBee Visibility Networks may also be managed by a low-cost Ethernet enabled router. Individual tags and tag data may be viewed as a stand-alone, web server from anywhere in the world. Each RuBee tag, if properly enabled, can be discovered and monitored over the World Wide Web using popular search engines (e.g., Google) or via the Visible Asset's .tag Tag Name Server.

Where a network connection 29 is utilized, it is contemplated that the network may be or include any one or more of, for instance, the Internet, an intranet, a LAN (Local Area Network), a WAN (Wide Area Network) or a MAN (Metropolitan Area Network), a frame relay connection, an Advanced Intelligent Network (AIN) connection, a synchronous optical network (SONET) connection, a digital T1, T3 or E1 line, Digital Data Service (DDS) connection, DSL (Digital Subscriber Line) connection, an Ethernet connection, an ATM (Asynchronous Transfer Mode) connection, FDDI (Fiber Distributed Data Interface) or CDDI (Copper Distributed Data Interface) connections and so forth. In this manner, the camera control unit 16 may be coupled to, for example, a remote computer 31 via the network connection 29 for remote access to the data and/or information transmitted to and from endoscope 12.

Another advantage of RuBee is that it can work well through liquids and metals and consumes less power. From a price perspective, RuBee and traditional RFID are similar in cost.

Endoscope transponder/transceiver 20 is coupled to a memory device 22. Memory device 22 is capable of storing and providing electronic representations of parameters of endoscope 12 to endoscope transponder/transceiver 20. Memory device 22 may be of any type that is programmable by such means as electrically, magnetically, by light frequencies or any type that is commonly known to those of ordinary skill in the art.

Also shown positioned in or on endoscope 12 is endoscope light source 21, endoscope electronics 23 and imager 25. In one embodiment, the endoscope light source 21 comprises an LED to provide illuminating light, for example, ahead of the distal end of the endoscope 12. Endoscope transponder/transceiver 20 receives electrical power via a wireless connection from camera transponder/transceiver 24. It is contemplated that the wireless coupling for transmission of the electrical power may comprise, for example, a resonate coupling arrangement, to function without need of any type of electrical storage device positioned on the medical instrument. In another embodiment, a reduced weight electrical storage device 19 may by positioned on the medical device to store a limited amount of electrical power in the event of a momentary disconnection from the wireless power coupling. In the second embodiment, the medical device would automatically start recharging when it enters the vicinity of a wireless power sending unit.

In one advantageous embodiment, camera transponder/transceiver (transmitter/receiver) 24 and endoscope transponder/transceiver (transmitter/receiver) 20 may comprise resonant transmitters and receivers. For example, a resonant transmitter may generate a resonant magnetic field. The transponder/transceivers may be "tuned" to the same frequency such that a strong resonant coupling occurs between camera transponder/transceiver 24 and endoscope transponder/transceiver 20. The resonant coupling in one advantageous embodiment, comprises evanescent stationary near-field. While the transponder/transceiver may comprise virtually any type of resonant structure, it is contemplated that in an advantageous embodiment, the electromagnetic resonant system may comprise dielectric disks and capacitively-loaded conducting-wire loops. This arrangement provides the advantages of a strong coupling for relatively large and efficient power transfer as well as relatively weak interaction with other off-resonant environmental objects in the vicinity.

Accordingly, in the resonant coupling embodiment, camera transponder/transceiver 24 generates a resonant magnetic field that is received by endoscope transponder/transceiver 20. Endoscope transponder/transceiver 20 then transmits electrical power to endoscope light source 21 and may further transmit electrical power to endoscope electronics 23 that may include imager 25. It is further noted that the endoscope comprises a shaft 27, either rigid or flexible that is inserted into a body cavity in which a medical procedure is to be performed. In one embodiment, the endoscope light source 21 is located in the handle portion of the endoscope (as illustrated in FIG. 1) and illuminating light is transmitted down a light path (in the shaft 27) to a distal end of shaft 27 to illuminate an area ahead of the shaft. The imager 25 may be positioned in the handle portion of the endoscope (as illustrated in FIG. 1) or at the distal end of the shaft 27 to receive or pick up reflected light to generate image data. The image data may then be transmitted to a camera control unit ("CCU") 16.

It should be noted that the image data is provided as a video image data stream comprising from about 30 to about 60 frames of data per second. This is possible as the resonant coupling allows for sufficient electrical power to be transmitted to the endoscope transceiver 208.

As mentioned above, camera head 14 is detachable from endoscope 12 and may be attached to other endoscopes. Camera head 14 is coupled to CCU 16 by cable 18. However, camera head 14 can be coupled to CCU 16 by, for instance; a cable connection, including analog, digital or optical; or a wireless connection. Cable 18 couples CCU 16 to camera head 14 and therefore with camera head transponder/transceiver 24. An annunciator 28 may be incorporated into CCU 16 for the purpose of communicating endoscope parameters to personnel operating the endoscope system 10. Annunciator 28 provides a means by which information concerning the endoscope is communicated to personnel operating the equipment. The annunciator may be a lamp, audible signal, alphanumeric display or other such communication device. Preferably, applicable endoscope parameters received by CCU 16 will subsequently be decoded and displayed on a video monitor for viewing by the endoscope system 10 operator. It is contemplated that memory device 22 may be queried through the present invention by an external computer (not shown) and stored data in memory device 22 retrieved for compilation and analysis. Power for the endoscope mounted circuitry, transponder/transceiver 20 and memory device 22 may be supplied by a power signal from camera head transponder/transceiver 24 derived from a signal from camera head 14, or from an external computer.

Components such as endoscope transponder/transceiver 20, camera head transponder/transceiver 24 and memory device 22, are selected and protected such that they will not be damaged during sterilization of either endoscope 12 or camera head 14. The sterilization may comprise any or all methods of high temperature, chemical or irradiation commonly used in the field. Components employed in endoscope transponder/transceiver 20, memory device 22 and camera head transponder/transceiver 24 must not be degraded by temperatures commonly employed in autoclaves, chemicals such as gluteraldehyde or ethylene oxide, gamma radiation, or any other such sterilization techniques known to those of ordinary skill in the art.

It is also contemplated that various sensors mounted in endoscope 22 will record on memory device 22 peak values that the endoscope 22 is exposed to. This will enable manufacturers and maintenance personnel to determine reasons for endoscope failures and periods for necessary maintenance based upon usage.

It is further contemplated that the endoscope system 10 user will be able to manually "mark" a particular endoscope with a "maintenance required" signal if it is determined by the user that maintenance of the particular endoscope is required. The "marking" can be facilitated by a button or switch locally mounted to the system. Alternatively, the "marking" may take place automatically by the system based upon predetermined criteria. The criteria may include, but is not limited to, elapsed time of use, a certain number of actuations upon receipt of exceeded peak value measurements, or an extended period of time since last maintenance. This "mark" will be transmitted by the endoscope to the CCU and may conspicuously appear on the video screen for future users to see.

The memory device 22 is write-protected such that only factory personnel and/or equipment can remove the "maintenance required" indication. This may be accomplished, for instance, by requiring specific equipment to erase the "maintenance required" indication or by means of a predetermined code that first must be input to enable the removal of the "maintenance required" indication. This will ensure that users of the endoscope system 10 utilize only factory-authorized personnel to repair and maintain the endoscope system 10, which will help to ensure a higher standard of service.

Figure 2:
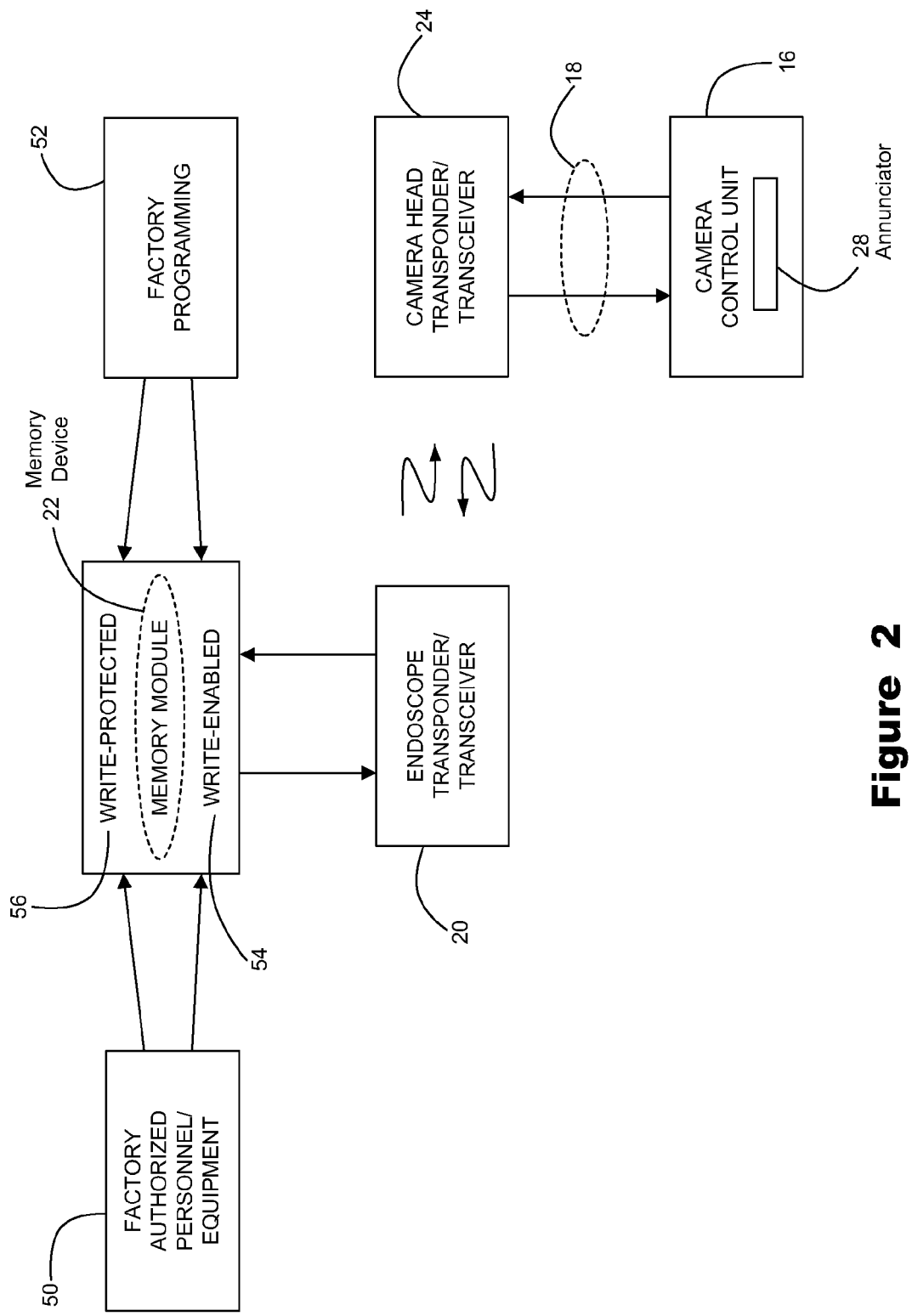
FIG. 2 illustrates the programming of the endoscope memory device and communication with the detachable camera head.

Referring to FIG. 2, memory device 22 stores and supplies electronic representations of endoscope parameters and endoscope use history data. These parameters and data provide a variety of information concerning the endoscope. Information stored in the endoscope would provide all required data for optimal use of the endoscope. In this way, the CCU 16, or other connected medical equipment, would not have to locally or remotely store and access data related to a vast array of different endoscopes. Moreover, as endoscopes are modified and/or improved, corresponding parameters and data are immediately accessible at the time of endoscope use.

The endoscope parameters are broadly classified as fixed or unchanging information. Examples of fixed or unchanging endoscope parameters may include endoscope model and serial number, image relay optics type (e.g., rod lens, fused quartz, fiber optic), endoscope size, optical properties such a field of view, signal processing data for use by the CCU 16 for video signal optimization, maintenance requirements and interval, settings information for other medical equipment (such as high intensity light sources or insufflators) which are connected and/or controlled by the CCU 16 via a communication bus or any variety of characteristics that may be useful in endoscope, video camera system and other medical equipment usage.

The endoscope use history data is broadly classified as variable or updateable. Examples of variable or updateable endoscope use history data may include, for instance, number of endoscope usages, time of each endoscope use, total time of endoscope operation, number of actuations and medical equipment (used with the endoscope) identification and settings information.

Memory device 22 locations are broadly classified as write-enabled 54 and write-protected 56. Memory device 22 can be capable of disallowing changes to memory locations until specified conditions are met. These conditions may be electrical such as requiring injection of a known signal or series of signals, or programmatic such as a password or any similar such method to prevent unauthorized alteration of the memory device locations. Write-protected locations store parameters that may be altered only during factory programming 52, or by factory authorized personnel/equipment 50. These endoscope parameters are generally, but not necessarily, fixed or unchanging as enumerated above. Write-enabled locations may be altered during factory programming 52, by factory authorized personnel/equipment 50, or with electronic representations of data received from the endoscope transponder/transceiver 20.

Endoscope transponder/transceiver 20 communicates with camera head transponder/transceiver 24 once the camera head transponder/transceiver 24 comes into close proximity. As previously described, power for the endoscope transponder/transceiver 20 is supplied from the camera head transponder/transceiver 24. Transceivers supplied with power in this manner typically have short ranges as compared to similar devices with their own power sources. It is anticipated that the effective range of transmission of the endoscope transponder/transceiver 20 and the camera head transponder/transceiver 24 may advantageously be very short. This is beneficial since an extensive transmission area could disadvantageously result in an endoscope communicating with an unrelated camera head or cause other communication problems with other equipment in the operating room. For example, if the RuBee signal format is utilized, it is contemplated that the signal range will extend from approximately 10 feet to approximately 50 feet.

Camera head transponder/transceiver 24 also exchanges signals with CCU 16 via cable 18. CCU 16 may present the received signals on annunciator 28. For example, data indicating that maintenance of the endoscope is required may be provided by endoscope transponder/transceiver 20 to camera head transponder/transceiver 24 which is forwarded to CCU 16 that, in turn, presents an alert to annunciator 28 that endoscope maintenance is required.

Figure 3:
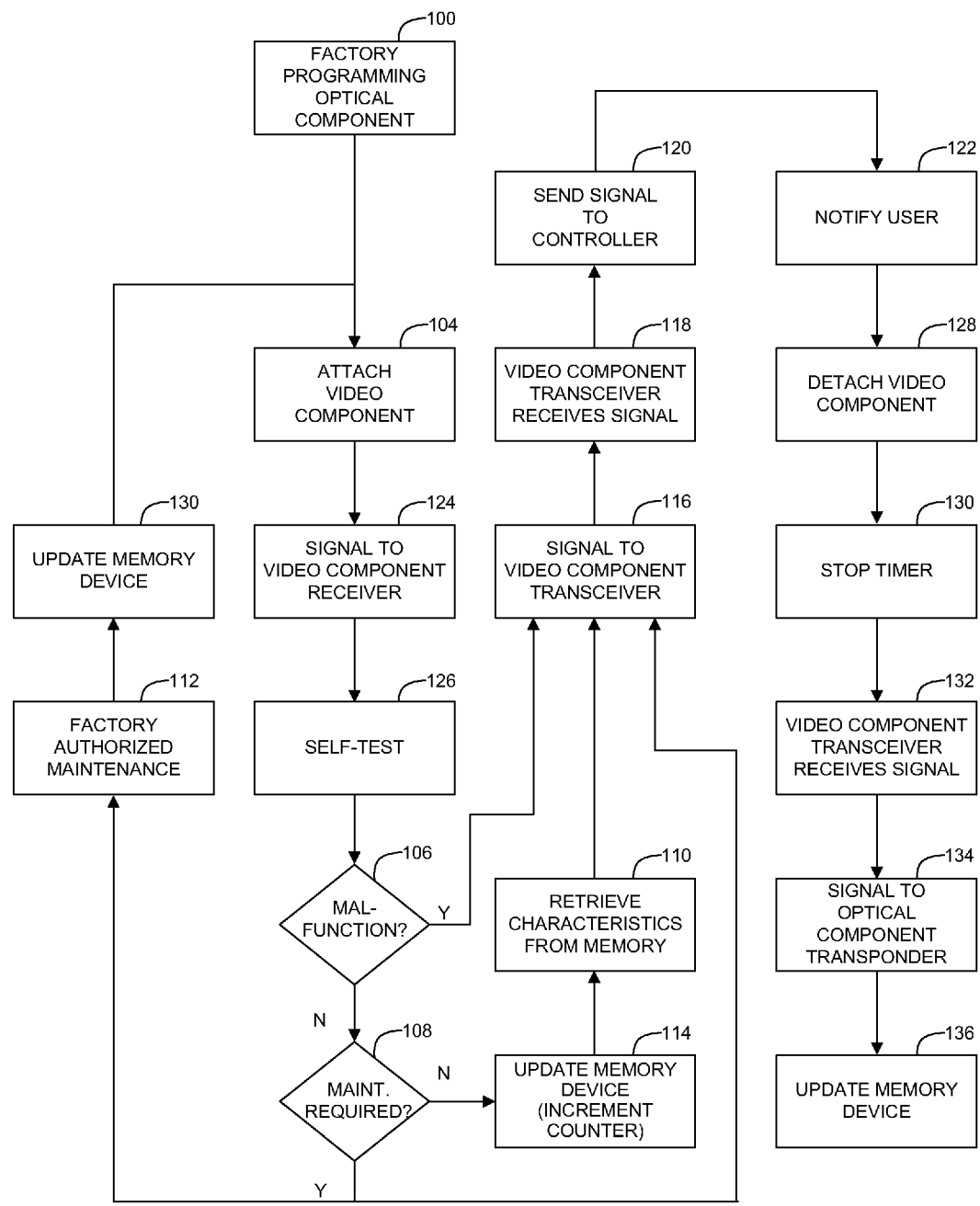
FIG. 3 illustrates a block diagram for implementing the method of the present invention.

FIG. 3 illustrates another application of the present invention. At 100, during manufacture of the endoscope, a memory device mounted in or on the endoscope is programmed with electronic representations of parameters and data specific to that particular endoscope 105. These parameters may include the optical properties, serial number, model number, maintenance schedule, required camera settings, required equipment settings, malfunction codes and other such characteristics and parameters. The memory device will have sufficient additional memory locations to store other data as described below.

Once a camera head is energized, that is, "powered on," a short-range wireless signal is radiated from the camera head transponder/transceiver. Upon the energized camera head being attached to a particular endoscope 110, the wireless signal radiating from the camera head transponder/transceiver powers the endoscope transponder/transceiver. Consequently, the endoscope transponder/transceiver energizes the endoscope memory device, which provides the electronic representation of the endoscope parameters to the endoscope transponder/transceiver with the camera head transponder/transceiver receiving the wireless signal containing the electronic representation of the endoscope parameters from the endoscope transponder/transceiver 115. The CCU, connected to the camera head, decodes the electronic representations of the endoscope parameters and thus "identifies" the endoscope in use. Specific information can then be communicated to the system user 120, such as, but not limited to, endoscope type/model or serial number. The communication may be a visual indicator, an alphanumeric display or printout, an audio signal or any such communication technique. Preferably, the information is displayed on the system video monitor. If the endoscope attached to the camera head does not have a transponder/transceiver and programmed memory device, the video system configuration will remain unchanged.

Once the endoscope is identified and the endoscope parameters are loaded to the CCU, the CCU analysis and increments a "times used" counter (data) 125 for tracking and updating the count of how many times the endoscope was used with an endoscope reader compatible video system. The updated use count data is then written to the endoscope memory device as modified endoscope use history data by means of the camera head transponder/transceiver and the endoscope transponder/transceiver 130.

The amount of time that an endoscope is in use determines the necessity for maintenance, as well as providing statistical data for factory use in design and marketing. Concurrent with the incrementing of the "times used" counter, the CCU also starts an elapsed time ("time in use") clock 135. The elapsed time continues to accumulate as long as the camera head is attached to the endoscope. Periodically, throughout the current use of the endoscope, the CCU, by means of the camera head transponder/transceiver and endoscope transponder/transceiver, updates the endoscope memory device 130 with modified endoscope use history data containing new accumulated "time in use" data 135. In this way, the total "time in use" corresponding to a particular use of the endoscope is stored in the endoscope memory device.

Based upon endoscope parameters extracted from the endoscope memory device, the maintenance status of the endoscope 140 is determined by the CCU. The maintenance requirements criteria, endoscope use history data and any other datum items required for the CCU to determine the current status of the endoscope was previously received by the CCU from the endoscope memory device at 115. If the CCU determines that endoscope maintenance is required 145, the maintenance related information is communicated to the user 150. The communication may be a visual indicator, an alphanumeric display or printout, an audio signal or any such communication technique. Preferably, the information is displayed on the system video monitor.

Depending upon the type of endoscope maintenance required, the user may, be provided the option to continue using the endoscope 160. If the user opts to continue, information pertaining to the continuation is then written to the endoscope memory device by means of the camera head transponder/transceiver and the endoscope transponder/transceiver 130. If the user opts not to continue endoscope use 165 or the continuation option 155 is not provided to the user, it is anticipated that the endoscope will be sent for factory authorized maintenance 170. When the maintenance is completed, the memory device is updated 105 so that the routine maintenance requirements are reset and the video system no longer reports that maintenance is required. The endoscope is again ready for camera head attachment 110 and use.

If endoscope maintenance is not required 175 at 140 or the user opts to continue using the endoscope 160 at 155, the CCU adjusts video processing settings 180 in order to optimize the video system according to endoscope parameters previously retrieved at 115. Additionally, other medical equipment, such as light sources or insufflators settings, may be optimized 180 according to endoscope parameters, as previously described.

Further information gathered, analyzed and compiled may be included in the endoscope use history data by the CCU for storage in the endoscope memory device 130. Endoscope use history data may include data on what camera head, CCU and other medical equipment was used with the endoscope (to include equipment serial numbers, model numbers, software revision numbers, etc.). Any information, which may be useful in determining how well an endoscope functioned, or under what conditions the endoscope functioned, could be included in the endoscope use history data. The endoscope use history data could later be retrieved for demographic or performance analysis purposes. An example is as follows. If a particular endoscope causes numerous CCUs to set exposure levels above a nominal value, this may indicate that the endoscope is not properly relaying images to the camera head. This CCU exposure level data would be included in the endoscope use history data and stored in the endoscope memory device. A review of the stored data would reveal this operational "trend," the endoscope could be inspected and, if necessary, repaired before a catastrophic failure occurs.

As previously described, periodically, the CCU updates the endoscope memory device 130 with modified endoscope use history data containing new accumulated "time in use" data 135. When the camera head is detached from the endoscope 190, the last accumulated "time in use" data will already have been stored in the endoscope memory device. The interval at which the "time in use" data is updated in the endoscope memory device would be frequent enough (i.e., every few minutes or every minute) to ensure the accuracy of the data prior to the camera head being detached from the endoscope.

Figure 4:
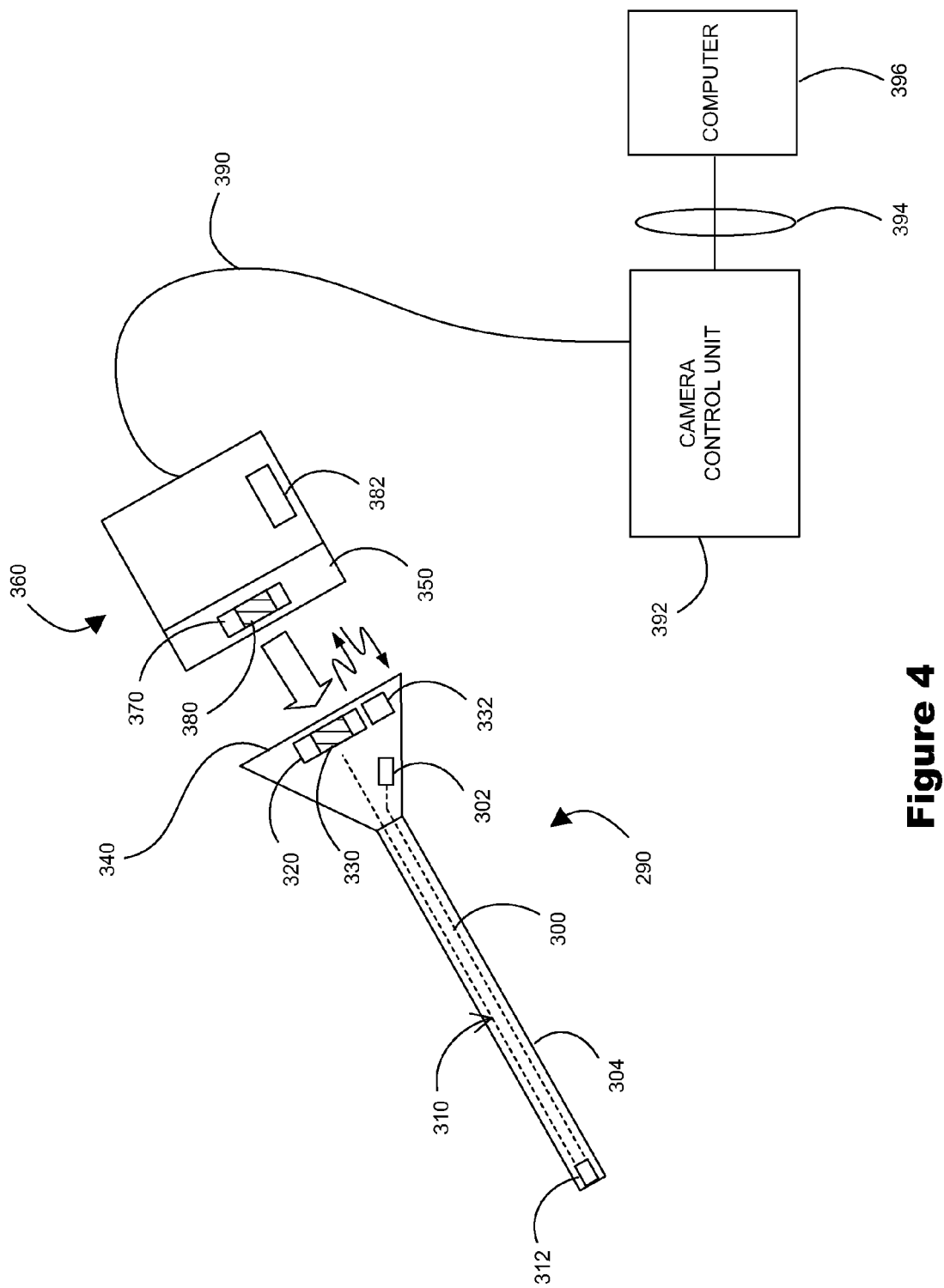
FIG. 4 illustrates an advantageous embodiment of the present invention according to FIG. 1.

FIG. 4 illustrates another advantageous embodiment of the present invention. An endoscope 290 houses an LED 302, a fiberoptic illumination conduit 300, an optical train 310, a wire coil 320 with a ceramic ferrite core 330, and control electronics 332. The endoscope 290 is provided with an axisymmetric connector 340 that has a shape similar to a traditional endoscopic eyecup, allowing it to rotate in a traditional coupling mechanism 350 attached to the camera head 360. Another wire coil 370 with core 380 and electronics 382 is positioned in the camera head 360. Power is supplied to the camera head coil 370 through the camera cable 390 and wirelessly transmitted across the camera-endoscope interface to the endoscopic wire coil 320 in much the same way as power is transmitted across coils in a transformer. The endoscope 290 can rotate freely in the coupling 350. In addition, the power to the camera head coil 370 can be disabled, making the camera head 360 compatible with traditional eyecup endoscopes.

The coupling mechanism 350 is designed to allow smooth and free rotation of the endoscope 290 relative to the camera head 360, while also providing a robust coupling which reliably maintains tight mating between the endoscope 290 and the camera head 360. Proper mating is important for reliable power transfer across the interface; the transformer efficiency drops off in a steep approximately linear fashion with increasing distance between the coils 320, 370. It is therefore crucial that mating remains solid and consistent during relative rotation. The transformer efficiency is also sensitive to parameters such as frequency, current, magnetic permittivity, materials, geometry, etc. H-bridges and electronics 332, 382 support the operation of the transformer.

Because this design requires no transfer of light or current at the coupling interface, it is also suitable for so-called chip-in-tip endoscopes where the imager 312, typically a CCD or a CMOS sensor, is positioned towards the tip of the endoscope. In this case, the camera head 360 would contain mainly electronics and effectively function as a handle for the surgeon to grip. The imager would be powered in the same way as the onboard light source. Such a modular design would not be backwards compatible with traditional endoscopic systems, but it would bring several advantages over designs which integrate optical, electrical, illumination, and camera subsystems into a single unit: 1) sensitive control electronics can be separated from the endoscope portion, possibly making sterilization simpler and more effective; 2) if either the handle portion or the endoscope portion fails, the failure will likely be confined to a single module and will therefore be easier to troubleshoot and repair; and 3) the system is less likely to break if the typically heavier handle portion can be separated from the endoscope portion during reprocessing and sterilization.

It is further understood that control electronics 332 may comprise any or all of the features discussed in connection with FIG. 1, such as, for example, a memory device 22 (FIG. 1), a power storage 19 (FIG. 1), and endoscope electronics 23 (FIG. 1). In this manner, the particular features and advantages of the system according to FIG. 1 are also applied to the advantageous embodiment illustrated in FIG. 4.

Also depicted in FIG. 4 are camera control unit 392, network connection 394 and computer 396, which again, function in accordance with the corresponding devices described in connection with FIG. 1.

Figure 5:
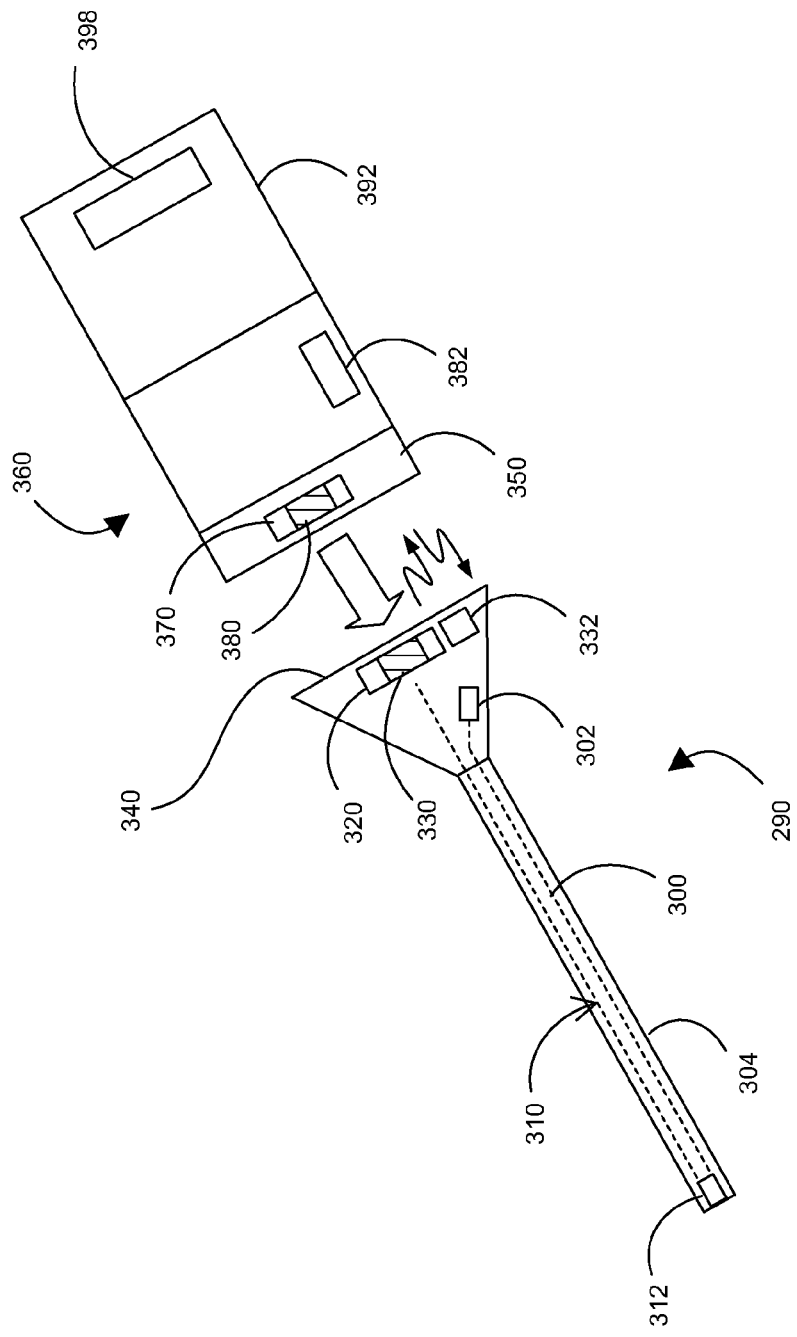
FIG. 5 illustrates an advantageous embodiment of the present invention according to FIG. 1.

FIG. 5 illustrates another embodiment of the present invention. The embodiment of FIG. 5 is similar to that described in connection with FIG. 4, however, the camera control unit 392 is integrated with camera head 360. The camera control unit 392 provides substantially the same functionality as previously described in connection with FIG. 4, however, the camera control unit 392 is provided either integral with camera 360 or is detachably mounted onto camera 360. In this manner, the system is a fully portable unit including the endoscope 290 and the camera 360 (having an integral camera control unit or having the CCU mounted thereon). It is contemplated that the image data received and processed by camera control unit 392 may be saved on, for example, a storage device (which may comprise a removable device such as a USB thumb drive and the like) in the camera control unit 392 and/or wirelessly transmitted to a display and/or remote storage device. The storage on the camera control unit may provide for storage of all of or any portion of a procedure to be documented. Additionally, the storage device may provide for buffering of the image data such that, in the event of a communication lapse, the image data may be transmitted upon reconnection.

The camera control unit 392 may also be provided with a rechargeable battery 398 that may be recharged by placing the camera head 360/camera control unit 392 into a charging cradle. Alternatively, the rechargeable battery may be removable such that only battery need be placed in the recharging cradle. Still further, it is contemplated that the camera head 360/camera control unit 392 may be configured to be plugged into a wall outlet to be recharged. In any event, the rechargeable battery 398 will wirelessly provide power to the endoscope as previously described herein. The display and/or remote storage may also be coupled to a network connection as previously described.

Although the invention has been described with reference to a particular arrangement of parts, features and the like, these are not intended to exhaust all possible arrangements or features, and indeed many other modifications and variations will be ascertainable to those of skill in the art. For example, there are many alternative ways of designing, building, and manufacturing this invention, including geometric and material changes, are possible without departing from the principle of the invention. Also, this invention is not limited to medicine but also applies to, for example, industrial endoscopy.

What is claimed is:

1. An endoscope video system for wirelessly powering an endoscope coupled to a detachable camera comprising:
    an endoscope having a first transceiver positioned thereon, the first transceiver receiving wireless energy;
    an endoscope coupling mechanism affixed to a proximal end of said endoscope;
    a camera having a second transceiver positioned thereon, the second transceiver wirelessly coupling to the first transceiver when brought in proximity thereto to transmit energy to the first transceiver;
    a camera coupling mechanism engagable with said endoscope coupling mechanism to mechanically couple said endoscope to said camera;
    wherein said endoscope further comprises a memory device positioned thereon and coupled to the first transceiver and wherein said memory device has endoscope parameter data and endoscope use history data stored thereon.

2. The endoscope video system of claim 1 wherein when said endoscope coupling mechanism engages with said camera coupling mechanism, whereby said endoscope is rotatable relative to said camera.

3. The endoscope video system of claim 1 further comprising an endoscope light source positioned on said endoscope, said endoscope light source coupled to and receiving electrical power from said first transceiver.

4. The endoscope video system of claim 3 wherein said endoscope further comprises a shaft having a distal and a proximal end, and wherein said endoscope light source is positioned in the shaft.

5. The endoscope video system of claim 4 wherein said endoscope light source is positioned at the distal end of the shaft.

6. The endoscope video system of claim 1 further comprising a camera control unit coupled to the said camera, said camera control unit receiving and processing the image data.

7. The endoscope video system of claim 6 further comprising a display coupled to said camera control unit, said display presenting said image data to a user.

8. The endoscope video system of claim 6 further comprising a network connection coupled to said camera control unit, wherein the image data is transmitted via said network connection to a remote location for display and/or storage.

9. The endoscope video system of claim 6 wherein said camera control unit is provided integral with said camera or is detachably mounted onto said camera.

10. The endoscope video system of claim 9 wherein said camera control unit further comprises a rechargeable battery.

11. The endoscope video system of claim 1 wherein said endoscope further comprises an energy storage device.

12. The endoscope video system of claim 1 wherein said first transceiver comprises a fist coil of wire and said second transceiver comprises a second coil of wire.

13. The endoscope video system of claim 12 wherein said first transceiver further comprises a first ferrite core and said second transceiver further comprises a second ferrite core.

14. The endoscope video system of claim 1 further comprising a camera control unit coupled to said camera, wherein said endoscope parameter data and endoscope use history data is transmitted from said endoscope to said camera control unit and said camera control unit generates modified endoscope use history data, which is transmitted to and saved on said memory device on said endoscope.

15. An endoscope video system for wirelessly powering an endoscope coupled to a detachable camera comprising:
- an endoscope having a first transceiver positioned thereon, the first transceiver receiving wireless energy;
- an endoscope coupling mechanism affixed to a proximal end of said endoscope;
- a camera having a second transceiver positioned thereon, the second transceiver wirelessly coupling to the first transceiver when brought in proximity thereto to transmit energy to the first transceiver;
- a camera coupling mechanism engagable with said endoscope coupling mechanism to mechanically couple said endoscope to said camera;
- a light source positioned on said endoscope, said light source coupled to and receiving electrical power from said first transceiver; and
- said light source generating illuminating light;
- wherein said endoscope further comprises a memory device positioned thereon and coupled to the first transceiver and wherein said memory device has endoscope parameter data and endoscope use history data stored thereon.

16. The endoscope video system of claim 15 wherein said endoscope further comprises a shaft having a distal and a proximal end, and wherein said light source is positioned in the shaft.

17. The endoscope video system of claim 16 wherein said light source is positioned at the distal end of the shaft.

18. The endoscope video system of claim 15 wherein said endoscope further comprises an energy storage device.

19. The endoscope video system of claim 15 wherein when said endoscope coupling mechanism engages with said camera coupling mechanism, whereby said endoscope is rotatable relative to said camera.

20. An endoscope video system for wirelessly powering an endoscope comprising:
- an endoscope having a shaft having a distal and a proximal end;
- a first transceiver positioned on said endoscope, the first transceiver receiving wireless energy;
- a controller having a second transceiver positioned thereon, the second transceiver wirelessly coupling to the first transceiver when brought in proximity thereto to transmit energy to the first transceiver;
- an imager positioned on said endoscope, said imager coupled to and receiving electrical power from said first transceiver;
- said imager generating image data;
- a light source positioned on said endoscope, said light source coupled to and receiving electrical power from said first transceiver;
- wherein said endoscope further comprises a memory device positioned thereon and coupled to the first transceiver and wherein said memory device has endoscope parameter data and endoscope use history data stored thereon.

21. The endoscope video system of claim 20 wherein said imager is positioned in the shaft.

22. The endoscope video system of claim 21 wherein said imager is positioned at the distal end of the shaft.

23. The endoscope video system of claim 20 wherein said light source is positioned in the shaft.

24. The endoscope video system of claim 23 wherein said light source is positioned at the distal end of the shaft.

25. The endoscope video system of claim 20 further comprising a display coupled to said controller and displaying said image data.

26. The endoscope video system of claim 20 further comprising a network connection coupled to said controller, wherein the image data is transmitted via said network connection to a remote location for display and/or storage.

27. The endoscope video system of claim 26 wherein said controller is detachably coupled to said endoscope.

28. The endoscope video system of claim 27 wherein said controller further comprises a rechargeable battery.

29. The endoscope video system of claim 20 wherein said endoscope further comprises an energy storage device.

30. The endoscope video system of claim 20 wherein said first transceiver comprises a fist coil of wire and said second transceiver comprises a second coil of wire.

31. The endoscope video system of claim 30 wherein said first transceiver further comprises a first ferrite core and said second transceiver further comprises a second ferrite core.

32. The endoscope video system of claim 20 wherein said endoscope parameter data and endoscope use history data is transmitted from said endoscope to said controller and said controller generates modified endoscope use history data, which is transmitted to and saved on said memory device on said endoscope.

* * * * *